United States Patent [19]

Hanssen

[11] Patent Number: 4,976,274
[45] Date of Patent: Dec. 11, 1990

[54] SURGICAL DRAPE AND A METHOD FOR ITS MANUFACTURE

[75] Inventor: Carl-Otto Hanssen, Kullavik, Sweden

[73] Assignee: Molnlycke AB, Goteborg, Sweden

[21] Appl. No.: 195,681

[22] Filed: May 11, 1988

[30] Foreign Application Priority Data

May 15, 1987 [SE] Sweden .............................. 87020095

[51] Int. Cl.⁵ ...................... A61B 19/00; A61B 19/08
[52] U.S. Cl. ...................................... 128/849; 128/855
[58] Field of Search ............... 128/849, 850, 851, 852, 128/853, 854, 855, 856; 136/244; 350/629

[56] References Cited

U.S. PATENT DOCUMENTS

| | | | |
|---|---|---|---|
| 3,335,719 | 8/1967 | Boucher | 128/855 |
| 3,503,391 | 3/1970 | Melges | 128/852 |
| 3,799,161 | 3/1974 | Collins | 128/854 |
| 4,080,963 | 3/1978 | Merry | 128/853 |
| 4,196,723 | 4/1980 | Moose, Jr. | 128/854 |
| 4,471,769 | 9/1984 | Lockhart | 128/849 |
| 4,607,631 | 8/1986 | Hanssen | 128/853 |
| 4,664,103 | 5/1987 | Martin | 128/852 |
| 4,688,563 | 8/1987 | Hanssen | 128/853 |
| 4,690,137 | 9/1987 | Starzmann | 128/849 |

FOREIGN PATENT DOCUMENTS 1397342 6/1975 United Kingdom .

Primary Examiner—Robert A. Hafer
Assistant Examiner—Michael Brown
Attorney, Agent, or Firm—Young & Thompson

[57] ABSTRACT

A surgical drape which is configured to enable a plurality of different types of surgical drape to be manufactured on one and the same machine. According to a first embodiment of the invention, the surgical drape includes a pair of mutually similar L-shaped parts (2, 3) which are joined together at least along the inner edges of the two pairs of legs (A, B) of the L-shaped parts (2, 3). According to another embodiment, the drape includes a pair of mutually similar U-shaped parts (22, 23) which are joined together at least along the inner edges of the leg and base portions of the U-shaped parts (22, 23).

10 Claims, 5 Drawing Sheets

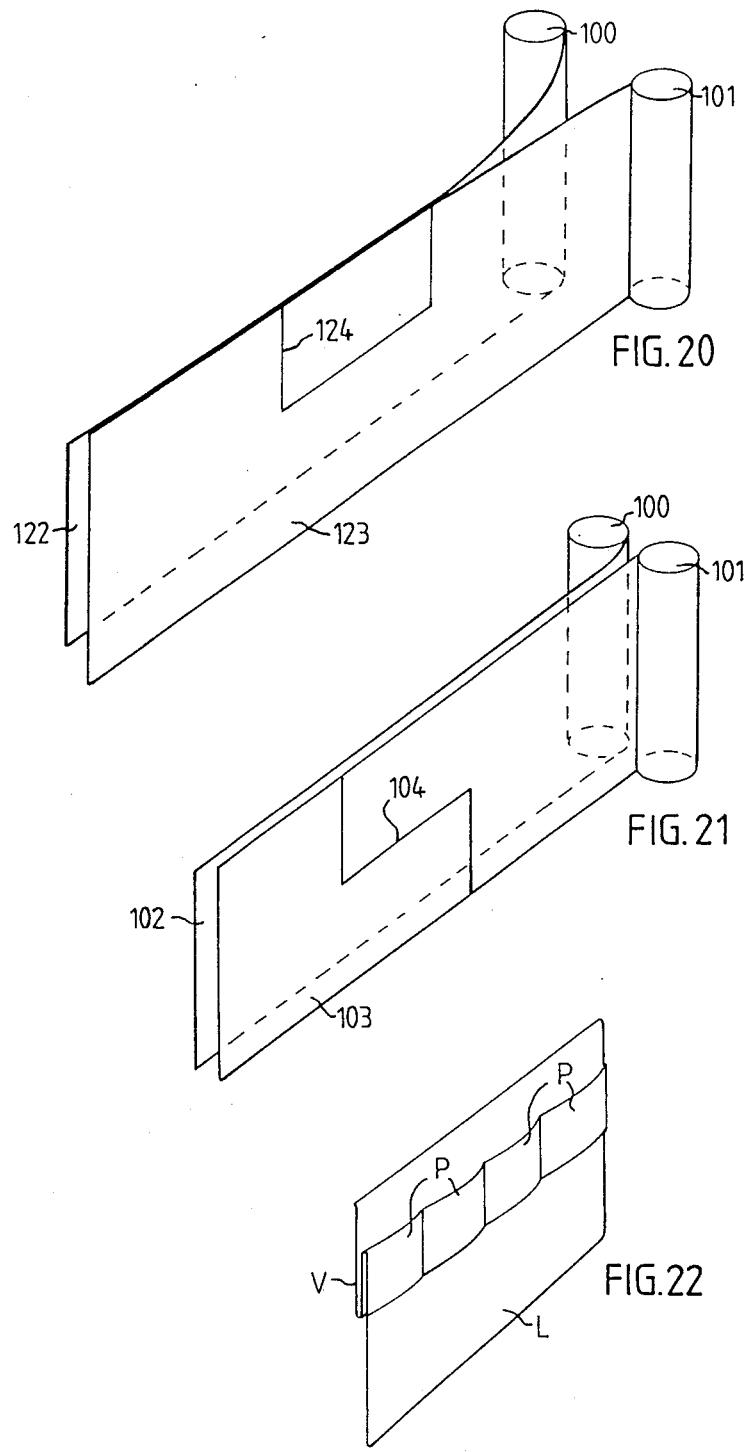

SURGICAL DRAPE AND A METHOD FOR ITS MANUFACTURE

The present invention relates to a surgical drape.

When performing surgical operations there are normally used at present surgical drapes which have either been produced particularly for the kind of operation concerned or which consist of a universal set of drapes comprising four separate surgical sheets or covers. Because the major part of the cost of producing a universal set of drapes resides in the cost of materials used, and due to the large series in which the sets can be produced, and because the sheets forming the sets can be produced with the aid of structurally simple machines, the purchase price of such sets is relatively low. The universal drape-set is less suitable from the aspect of arrangement, since the sheets take longer to arrange prior to performing surgery than do the special-duty drapes, and furthermore the standardized dimensions of the sheets of a set of drapes sometimes means that more material than necessary is used for a surgical operation.

The object of the present invention is to provide a surgical drape which although being manufactured especially for a particular type of surgical operation is still favourable from the aspect of manufacture. The object is achieved in accordance with the invention with a surgical drape as described hereinafter.

The invention is based upon the concept of dividing the covering function of the drape into three separate parts, namely covering of the operating table and also of peripheral equipment, such as an anaesthetists stand or arch; basic covering of the patient; and particular covering of the surgical areas, wherewith in one favourable application of the inventive surgical drape the drape need only fulfill the two first mentioned functional requirements and is thus intended to co-act with specially designed surgical drapes which fulfill the special requirements which each type of surgical operation places on the covering drape within the surgical area with regard to the absorbency of the drape, its freedom from fluff or down, the ability of the drape material to resist wear, etc.

The inventive configuration of the surgical drape enables not less than six mutually different types of surgical drape to be produced on one and the same machine, with only small and simple changes in the setting of the machine. It will be understood, however, that the inventive surgical drape can also be provided with conventional working apertures through which surgical manipulations can be carried out.

So that these and other features will be more readily understood and the advantages afforded by the invention made apparent, the invention will now be described in greater detail with reference to a number of exemplifying embodiments of the inventive surgical drape and the inventive method for its manufacture and with reference to the accompanying drawings; in which FIG. 1 illustrates a first embodiment of the inventive surgical drape, with the drape unfolded;

FIGS. 20 and 21 illustrate schematically methods for manufacturing embodiments of the inventive surgical drape; and FIG. 22 illustrates the formation of pockets in a surgical drape.

Figure 1:
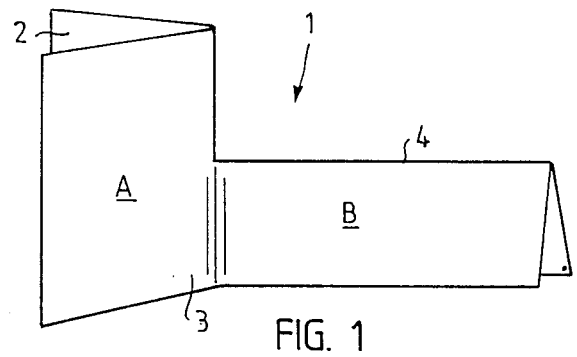

The surgical drape illustrated in FIG. 1 comprises two L shaped parts 2, 3 which are joined together along the inner edges 4 of pairs of limbs A and B, which form the parts 2 and 3. The parts are preferably either heat-welded together or glued together. Naturally, the parts 2, 3 may be configured from a single piece of material. FIG. 1 illustrates the drape prior to folding the same to its packaging configuration.

Figure 2:
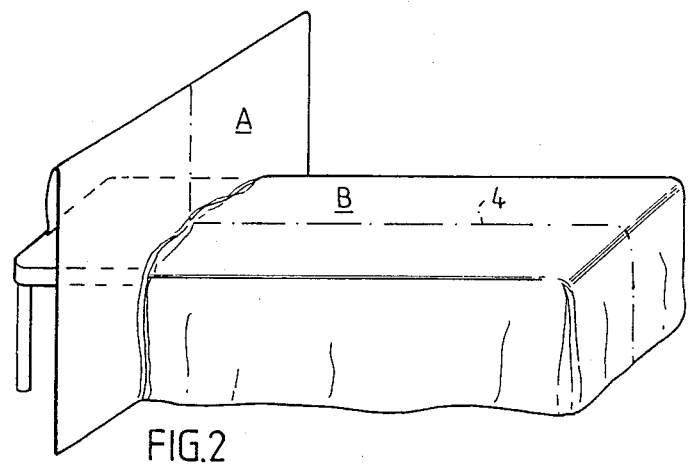
FIG. 2 illustrates the drape of FIG. 1 in use, with the drape covering an operating table and an anaesthetists arch or stand.

FIG. 2 illustrates the surgical drape 1 in one position of use, in which the pair of legs B cover an operating table and form vertical shielding walls around three sides of the table, and the pair of legs A hang over an anaesthetists arch or stand to shield the anaesthetist and his staff from the surgical area. The joint 4 is shown in chain lines.

It may at times be desirable to use for the pair of legs A a material which is different to that used in the pair of legs B, since the requirements placed on the material used to screen the anaesthetist are different to those placed on the material used to cover the patient. The material from which the patient-covering part of the drape is made should be absorbent and should have a dull, slightly rough surface so that the material will not shine and so that surgical instruments which are placed on this part of the drape will not slide about. Furthermore, the drape surface which faces the patient should not be a plastic surface. One requirement placed on the part of the drape which is positioned over the anaesthetists arch is that the material has a relatively high tensile strength. Furthermore, this part of the drape need not be absorbent and can be made entirely of plastic.

Figure 3:
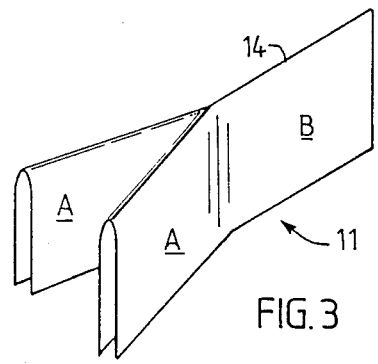
FIG. 3 illustrates the drape of FIG. 1 in a different position of use than that shown in FIG. 2.

The drape 11 illustrated in FIG. 3 is intended for surgery in the crotch area of a patient, the pair of legs B in this case covering the crotch area of the patient and the pair of legs A being wrapped around respective legs of the patient. It will of course be understood that the FIG. 3 embodiment is produced merely by folding the FIG. 1 embodiment such that the legs A are joined by a portion of edge 14 which is oppositely folded from the corresponding portion of edge 4 of FIG. 1.

The surgical drape 21 differs from the surgical drape illustrated in FIGS. 1 and 3, insomuch as the drape 21 also includes a second pair of legs A, the dimensions of the three pairs of legs being contingent on the particular use for which the drape is intended. As in the case of FIG. 1, the leg and base portions A and B have inner edges 24 that are mutually joined to each other. In addition to a combination of the areas of use of the drapes 1 and 11, in which combination the one pair of legs A is used to screen the anaesthetist and his staff and the other pair of legs A is folded in beneath the patient's legs, the drape 21 can be configured, e.g. for gynaecological operations, in which the pair of legs A are wrapped around the legs of a patient and the pair of legs B are used respectively to cover the upper side and the under side of the patient's crotch.

Figure 5:
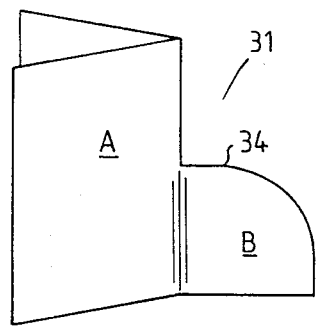

The surgical drape 31 illustrated in FIG. 5 is intended to cover at least the hairy part of a patient's head and has a different configuration to the drape 1, in that the legs of pair B are not rectangular in shape. As shown in FIG. 5, the inner edges of the legs of leg pair B are curved and merged with the similarly curved end edges of the legs of pair B. Furthermore, the joint 34 extends along the inner edges of the pairs of legs A and B and along the end edge of the pair of legs B, up to the outer edge thereof. Thus, when the pair of legs B are unfolded they will have a hemi-spherical shape and can be placed over the head of a patient.

The aforedescribed surgical drapes are manufactured from a material which is essentially impervious to bacteria. A suitable material in this regard will comprise a two-layer, or multi-layer fibre-cloth and plastic film laminate, although it may comprise solely plastic film or fibre cloth. Furthermore, an advantage is afforded when the material is thermoplastic, since it is then possible to cut out and weld together the various parts of the drape in a single manufacturing step.

The requirements placed on the properties of the material which covers the vicinity of the surgical area, i.e. properties such as wet strength and absorbency, are greater than those placed on the remaining parts of a drape. As beforementioned, one area of application, the described surgical drapes are intended to be used together with special-duty drapes which have been adapted to the particular requirements which the intended surgical operation places on the properties and exposed surface of the material around the body area in which the operation is performed. To this end, the inventive surgical drapes are provided with cut-outs which expose the intended surgical areas. By surgical area is meant here the area of a surgical drape on which the aforesaid special requirements are placed on the covering material.

Figure 6:
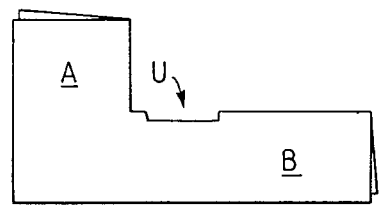
FIGS. 6-11 illustrate six different embodiments of an inventive surgical drape provided with apertured regions for exposing particular surgical areas.
Figure 7:
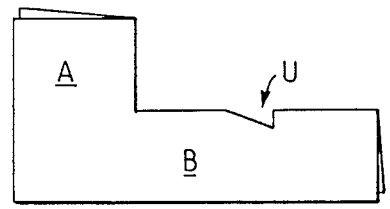
Figure 8:
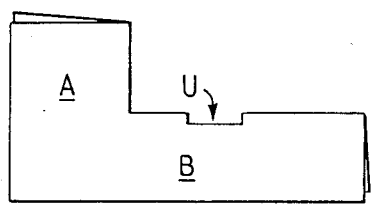
Figure 9:
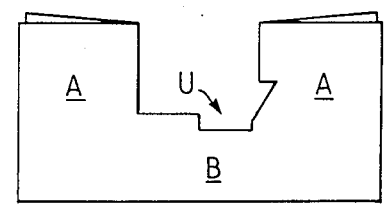
Figure 10:
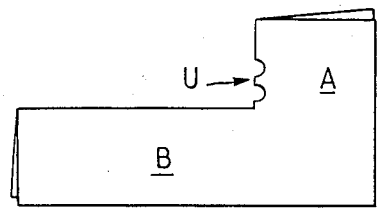
Figure 11:
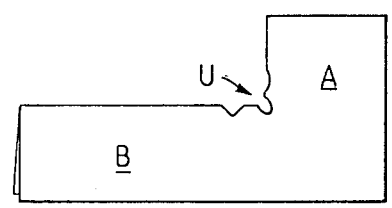
Figure 12:
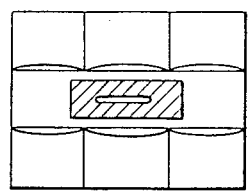
FIGS. 12-19 illustrate special-duty drapes which are intended for use together with any of the drapes illustrated in FIGS. 6-11.
Figure 13:
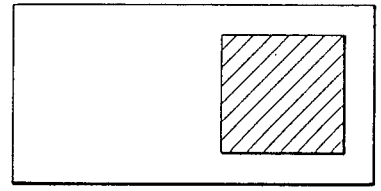
Figure 14:
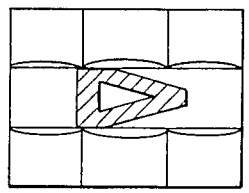
Figure 15:
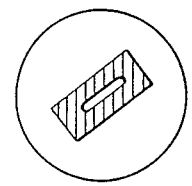
Figure 16:
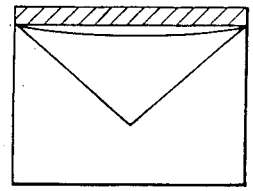
Figure 17:
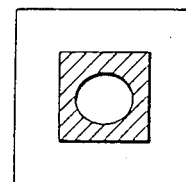
Figure 18:
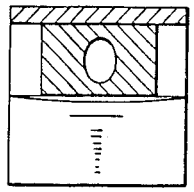
Figure 19:
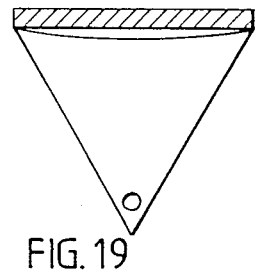

FIGS. 6-11 illustrate examples of surgical drapes of the type described with reference to FIGS. 1-4, in which cut-outs U have been formed in conjunction with cutting out the surgical drapes, so as to expose the surgical areas of several types of surgical operations or surgical procedures. For example, FIG. 6 illustrates a surgical drape which is suitable for use when performing thorax surgery (chest, heart, lungs); FIG. 7 illustrates a surgical drape which is suitable for use when performing laparoscopy (a window in the abdominal cavity); FIG. 8 illustrates a surgical drape which is suitable for use when performing laparotomy (abdominal cavity, stomach); FIG. 9 illustrates a surgical drape which is suitable for use when performing gynaecological surgery; FIG. 10 illustrates a surgical drape which is suitable for use when performing gynaecological surgery, TUR (transuretal resection, e.g. the removal of prostate tumours) and cystoscopy; and FIG. 11 illustrates a surgical drape which is suitable for use in TUR-surgery with suprapubis (with an additional drainage opening externally of the pubic bone). FIGS. 12-19 illustrate examples of special-duty surgical drapes which are intended to be used together with any of the surgical drapes illustrated in FIGS. 6-11, for covering the surgical areas exposed by the U-shaped cutouts. These drapes are preferably placed in position at the time of performing the operation, since mutually different surgical manipulations or procedures may be required for mutually different patients within the intended surgical area, which also means that mutually different drapes are required. However, it may be an advantage to attach the special-duty drapes to a surgical drape configured for common surgical operations at the time of manufacturing the drapes.

Suitable methods of manufacturing the surgical drapes illustrated in FIGS. 1-11, the legs of which drapes are thus made of one and the same material, will now be described with reference to FIGS. 20 and 21. According to the method illustrated in FIG. 21, there are drawn from two spools 100 and 101 two material webs 102 and 103 which extend parallel with one another and in mutual covering abutment with each other. A step-like cut 104 is made in the webs or lengths and the mutually opposing cut edge-surfaces of respective webs 102 and 103 are joined together in some suitable fashion. When the webs comprise a thermoplastic material, the cuts and joints can be made with the aid of a knife or punch which includes on each side heating elements which are urged against the cut edge-surfaces when making the cuts. However, the cut surfaces can be joined together in many different ways, e.g. by first establishing a glue joint and then forming the step-like cut with the aid of the knife, while therewith entering the glue joint centrally so that the cut edge-surfaces of the following surgical drape are joined together. The described methods of joining respective surfaces are therefore not restrictive of the invention.

Subsequent to forming the step-like cut and joining together the cut edge-surfaces of the webs, a cut is made in both webs 102, 103 at right angles to the direction of web feed and at a suitable distance from the step-like cut. This will result in two surgical drapes of the kind illustrated in FIG. 1.

Although it is possible to provide the cut-out U while controlling the aforesaid knife or punch in a different manner, the U-shaped cut-out is preferably made after this working step in order to prevent control of the knife from becoming too complicated.

Figure 4:
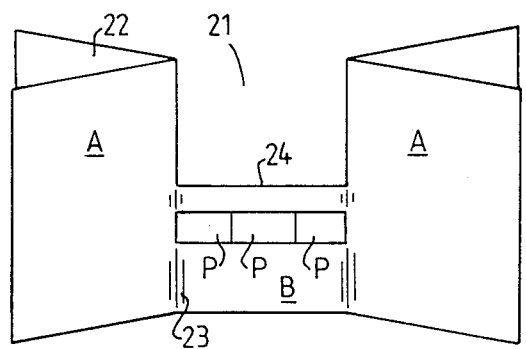
FIGS. 4 and 5 illustrate other embodiments of an inventive surgical drape.

The manufacture of a surgical drape of the kind illustrated in FIG. 4 is shown schematically in FIG. 20 and differs from the method described with reference to FIG. 21 in that the cut 124 is U-shaped and in that the cut edges are only joined together on one side of the knife or punch.

The devices used to advance the material webs and to shape the cut-outs and join the cut surfaces together have not been shown in FIGS. 20 and 21, the sole purpose of which is to illustrate the manufacturing principles applied when producing the inventive surgical drape. However, the inventive methods permit the use of simple components and uncomplicated component control means; for example the cutting means need only be capable of adjustment to provide a step-like or U-shaped cut and the surface joining means need only be capable of joining together straight surfaces, and consequently the manufacturing line described with reference to FIGS. 20 and 21 can be constructed from commercially available components.

The rectangular piece of material removed when producing a surgical drape of the kind illustrated in FIG. 4 can be used to provide instrument pockets on some suitable part of the surgical drape, as illustrated schematically in FIG. 4, which shows an elongated piece of material attached in some suitable manner to the leg B, with the aid of a longitudinally extending join and four transverse joins, to form three pockets P.

Another method of forming pockets P is illustrated schematically in FIG. 22, front which it will be seen that a piece of the drape material L is provided with pleats or folds V and that vertical joins are made along the side edges of the resultant pockets. It will be seen in this regard that the pockets illustrated in FIG. 4 can be provided in an analogous manner, if, when manufacturing in accordance with FIG. 20, the part of the cut which extends parallel with the web direction is not made and if this part of the cut merely constitutes a join line, wherewith the U-shaped parts of the webs 122, 123 above the join line thereof can the folded down, pleated and provided with separate vertical joins.

Thus, the invention enables several types of surgical drapes suitable for various types of surgical operations to be produced from the basic type of surgical drape illustrated in FIG. 1, by making small changes to the basic configuration and/or to the join lines. Furthermore, the configuration of this basic drape form enables all of the said drapes to be manufactured on the same machine, while the fact that only small changes in machine settings are required means that the time taken to switch from the manufacture of one drape form to another is relatively short. This enables the inventive surgical drape to be manufactured in small numbers at competitive prices.

I claim:

1. A surgical drape comprising two identically shaped sheet parts each having substantially the form of an L, said sheet parts each having two limbs extending perpendicularly relative to each other, said limbs having inner edges, the inner edges of said limbs of one said sheet part being joined to the inner edges of said limbs of the other said sheet part.

2. A surgical drape according to claim 1, in which each L-shaped part (2, 3) is produced in one piece.

3. A surgical drape according to claim 1, in which the end edges and the inner edges of one pair of legs (B) are joined together and provided with a curved shape so as to form a hemispherical configuration for placing the drape over a patient's head.

4. A surgical drape according to claim 1, in which the drape includes cut-outs (U) which expose surgical areas.

5. A surgical drape according to claim 1, in which the drape has instrument pockets (P).

6. A surgical drape according to claim 1, in which the pairs of legs (A, B) of the L-shaped parts are made of mutually different materials.

7. A surgical drape comprising two identically shaped sheet parts each having substantially the form of a U, said sheet parts each having a base portion and two leg portions extending perpendicularly from the base portion, said leg and base portions having inner edges, the inner edges of said leg and base portions of one said sheet part being joined to the inner edges of said leg and base portions of the other said sheet part.

8. A surgical drape according to claim 7, in which each U-shaped part (22, 23) is produced in one piece.

9. A surgical drape according to claim 7, in which the drape includes cut-outs (U) which expose surgical areas.

10. A surgical drape according to claim 7, in which the drape has instrument pockets (P).

* * * * *